United States Patent [19]

Fouquet

[11] 4,379,124

[45] Apr. 5, 1983

[54] REACTOR MADE FROM STEEL WITH PARTICULARLY HIGH RESISTANCE TO THE EFFECTS OF OXO SYNTHESIS AND METHOD OF PREPARING STEEL FOR USE IN CONSTRUCTING AN OXO REACTOR

[75] Inventor: Raymond Fouquet, Paris, France

[73] Assignee: Produits Chimiques Ugine Kuhlmann, Courbevoie, France

[21] Appl. No.: 246,680

[22] Filed: Mar. 23, 1981

Related U.S. Application Data

[63] Continuation of Ser. No. 60,872, Jul. 26, 1979, abandoned.

[30] Foreign Application Priority Data

Sep. 1, 1978 [FR] France ................................ 78 25261

[51] Int. Cl.³ ............................................. B01J 19/02
[52] U.S. Cl. ................................. 422/240; 75/126 C; 75/129
[58] Field of Search ............................... 422/240–242, 422/310; 75/126 C, 129; 261/DIG. 65

[56] References Cited

U.S. PATENT DOCUMENTS

| | | | |
|---|---|---|---|
| 2,109,118 | 2/1938 | Naumann | 422/240 X |
| 2,339,368 | 1/1944 | Bagsar | 422/240 X |
| 3,553,004 | 1/1971 | Schnedler | 75/126 C X |
| 3,957,442 | 5/1976 | Yamamoto et al. | 422/224 X |
| 4,019,930 | 4/1977 | Aylward | 75/126 C X |
| 4,072,470 | 2/1978 | Tsuto et al. | 422/242 |
| 4,089,679 | 5/1978 | Zecman | 75/126 C |
| 4,222,771 | 9/1980 | Oda et al. | 75/126 C X |
| 4,269,791 | 5/1981 | Hills | 261/DIG. 65 |

FOREIGN PATENT DOCUMENTS

920417 3/1963 United Kingdom .

*Primary Examiner*—Richard L. Chiesa
*Attorney, Agent, or Firm*—Sigalos & Levine

[57] ABSTRACT

The invention relates to the manufacture of reactors for Oxo synthesis which are constructed of steel having a Brinell hardness of less than 300 and containing 1 to 6% chromium and 0.4 to 0.7% molybdenum.

8 Claims, 1 Drawing Figure

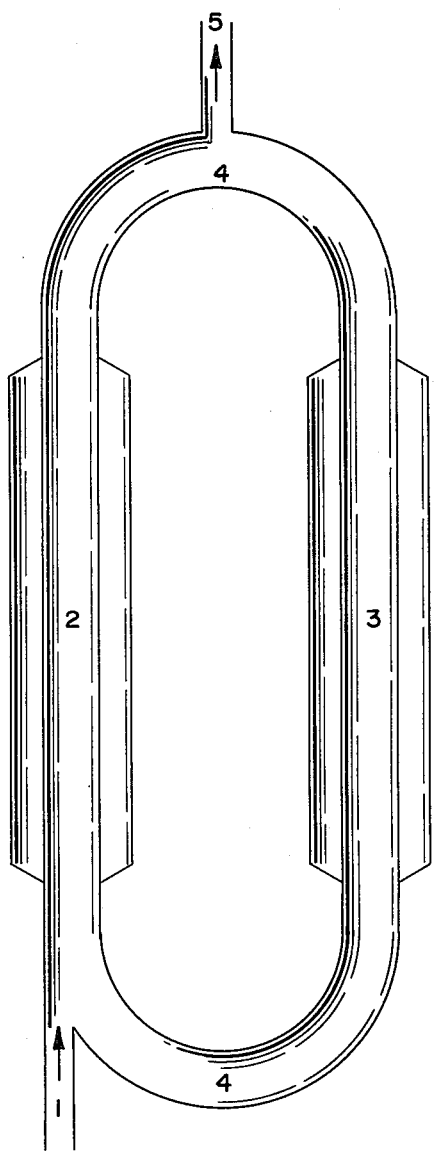

REACTOR MADE FROM STEEL WITH PARTICULARLY HIGH RESISTANCE TO THE EFFECTS OF OXO SYNTHESIS AND METHOD OF PREPARING STEEL FOR USE IN CONSTRUCTING AN OXO REACTOR

This application is a continuation application of prior application Ser. No. 060,782 filed July 26, 1979 and now abandoned.

BACKGROUND OF THE INVENTION

This invention applies to Oxo synthesis reactors and specifically to steels which are particularly adapted for the manufacture of reactors capable of resisting the parasitic effects of Oxo synthesis. The term "reactor" means the entire apparatus in which the reaction cycle is carried out. The invention also relates to the reactors made from these steels.

Oxo synthesis is known as the hydroformylation reaction which consists in reacting a mixture of carbon oxide and hydrogen with an olefin containing "n" carbon atoms in the presence of a catalyst which is usually cobalt-based. In the course of this reaction, aldehydes and alcohols containing "n+1" carbon atoms are formed.

This reaction is carried out in reactors of known design and dimensions which must withstand high pressures. One type of reactor which is suitable for this reaction is described in British Pat. No. 920,417. These reactors are generally made from ordinary steel, like any other reactor which is required to withstand high pressures.

However, in use, it is found that after a certain period of service, which can vary from several months to two years, cracks and occasionally serious fractures occur in these reactors which can cause grave accidents when these defects occur in an industrial plant required to operate under pressures of several hundred bars.

Although the exact reasons for these defects are not presently known, it is believed that they are of both chemical and metallurgical origin.

In the latter case, in particular, they could be due to the use of an unsuitable metal. The phenomena of corrosion resulting from the Oxo reaction products and/or from the reaction itself which cause the metal of the reactor to become fragile are not at all well understood, and therefore this supposition is the result of research carried out with a view to finding an alloy for producing a reactor in which the Oxo reaction could be performed with the maximum safety and without danger of premature wear of the reactor.

SUMMARY OF THE INVENTION

This invention, which is the result of such research, relates to a reactor for Oxo synthesis made from a steel which is characterized in that it has a Brinell hardness of less than 300 and contains 1 to 6% chromium and 0.4 to 0.7% molybdenum. Apart from the essential metals chromium and molybdenum, the steels to which the invention relates may also contain the metals usually found in steel alloys, such as manganese, silicon, etc., without any particular advantage or disadvantage. However, it has been found that steel which is free from vanadium is easier to use. Steels which are particularly suitable for the manufacture of Oxo reactors are steels of grades P11, P5, P5b, P5c according to the standard ASTM A 335.

Thus, the present invention relates to a reactor for carrying out Oxo synthesis comprising vertical tubes and means coupling the tops and bottoms of said vertical tubes, said tubes and coupling means being formed of steel having a Brinell hardness of less than 300 and containing 1-6% chromium and 0.4-0.7% molybdenum.

The invention also relates to a method of preparing steel for use in constructing a reactor in which Oxo synthesis is carried out comprising the steps of forming said steel with a Brinell hardness of less than 300 and containing 1-6% chromium and 0.4-0.7% molybdenum.

BRIEF DESCRIPTION OF THE DRAWING

These and other objects and advantages of the present invention will be disclosed in the course of the following specification, reference being had to the accompanying drawing which is a schematic representation of a reactor constructed with steel formed in accordance with the present invention.

DETAILED DESCRIPTION OF THE PREFERRED EMBODIMENT

As shown in the drawing, the reactor generally comprises two vertical tubes 2 and 3 connected to each other at the top and bottom thereof by two loop tubes 4. The reagents are generally introduced at the base of one of the vertical tubes 2 through inlet 1 and circulate in a closed circuit through the apparatus. The reaction products are usually recovered at the top of the reactor such as, for example, by tubing 5. The drawing, which is given as a guide to illustrate the principle of the apparatus, is subject to modifications, particularly with regard to the arrangement, form and diameter of the loop tubes 4.

Although a single steel meeting the requirements set forth earlier is suitable for the manufacture of the entire reactor, two different types of steel may be used, distributed as follows:

The straight parts of reactor are made from a steel containing 1 to 3% chromium and 0.4 to 0.7% molybdenum, e.g. grade P11 steel according to ASTM A 335 is suitable for this type of application, whereas the curved parts, located specifically at the loops connecting the vertical tubes, are made from a steel containing 3 to 6% chromium and 0.4 to 0.7% molybdenum, e.g. steels of grades, P5, P5b and P5c according to ASTM A 335 are suitable for this type of application. As an illustration of the invention, a reactor as shown in the accompanying drawing, with which hydroformylation of 8 to 10 tonnes/hour of olefins can be carried out at pressures of 200 to 300 bars, has been operating for 7 years without showing any signs of deterioration. The straight parts of this reactor consist of grade P11 steel according to ASTM A 335 and the curved parts are made from grade P5 steel according to ASTM A 335.

Thus, there has been disclosed a novel reactor so constructed that it is not subject to the effect of corrosion which causes cracks and fractures found in the reactors normally used for Oxo synthesis.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An oxo reactor for carrying out oxo synthesis comprising:
   a. vertical tubes,
   b. means coupling the tops and bottoms of said vertical tubes, said tubes and coupling means being formed of steel having a Brinell hardness of less than 300 and including in said steel 1-6% chromium and 0.4-0.7% molybdenum,
   c. inlet means for introducing the oxo reagents into the reactor and structured to result in immediate mixing of said reagents introduced into the reactor, and
   d. the steel used in making said coupling means being different from the steel used in making said vertical tubes and having a higher chromium content.

2. A reactor as in claim 1 wherein:
   a. said vertical tubes are made from a steel containing 1-3% chromium and 0.4-0.7% molybdenum, and
   b. said coupling means are made from steel containing 3-6% chromium and 0.4-0.7% molybdenum.

3. A reactor as in claim 2 wherein said steel is free from vanadium.

4. A reactor as in claim 3 wherein there are two of said vertical tubes coupled at the top and bottom by said coupling means.

5. A reactor as in claim 4 further comprising:
   a. a single inlet at the bottom of one of said vertical tubes for introducing the oxo reagents into the reactor and structured to result in immediate mixing of said reagents introduced into the reactor, and
   b. a single reaction product recovery outlet at the top of the reactor.

6. A method of constructing an oxo synthesis reactor comprising vertical tubes and means coupling the tops and bottoms of said tubes, said method comprising the steps of:
   a. forming said vertical tubes and coupling means of steel with a Brinell hardness of less than 300,
   b. including in said steel 1-6% chromium and 0.4-0.7% molybdenum, and
   c. the steel used in making said coupling means being different from the steel used in making said vertical tubes and having a higher chromium content.

7. A method as in claim 6 wherein said steel contains 1-3% chromium and 0.4-0.7% molybdenum, and is used for making said vertical tubes.

8. A method as in claim 6 wherein said steel contains 3-6% chromium and 0.4-0.7% molybdenum, and is used for making said coupling means.

* * * * *